(12) United States Patent
Arno

(10) Patent No.: US 7,925,450 B2
(45) Date of Patent: Apr. 12, 2011

(54) PHOTOMETRICALLY MODULATED DELIVERY OF REAGENTS

(75) Inventor: Jose I. Arno, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 12/773,666

(22) Filed: May 4, 2010

(65) Prior Publication Data

US 2010/0217415 A1  Aug. 26, 2010

Related U.S. Application Data

(63) Continuation of application No. 12/120,101, filed on May 13, 2008, now Pat. No. 7,711,496, which is a continuation of application No. 11/445,755, filed on Jun. 2, 2006, now Pat. No. 7,373,257, which is a continuation of application No. 11/157,760, filed on Jun. 21, 2005, now Pat. No. 7,058,519, which is a continuation of application No. 10/641,576, filed on Aug. 14, 2003, now Pat. No. 6,909,973, which is a continuation-in-part of application No. 10/402,759, filed on Mar. 28, 2003, now Pat. No. 7,063,097.

(51) Int. Cl.
 *G06F 19/00* (2006.01)
(52) U.S. Cl. ............. 702/24; 702/31; 702/32; 702/127; 250/343
(58) Field of Classification Search .................. 702/22, 702/24, 28, 30, 31, 32, 127; 366/131, 132; 438/7, 14, 15, 16, 17, 54, 200, 758; 250/343, 250/345
See application file for complete search history.

(56) References Cited

U.S. PATENT DOCUMENTS

| 3,342,199 | A |   | 9/1967  | McEvoy           |         |
|-----------|---|---|---------|------------------|---------|
| 4,042,344 | A |   | 8/1977  | Callcott et al.  |         |
| 4,275,752 | A |   | 6/1981  | Collier et al.   |         |
| 4,564,761 | A | * | 1/1986  | Buckwald et al.  | 250/341.4 |
| 4,647,777 | A |   | 3/1987  | Meyer            |         |
| 4,705,669 | A |   | 11/1987 | Tsuji et al.     |         |
| 4,768,291 | A | * | 9/1988  | Palmer           | 34/443  |
| 4,816,294 | A |   | 3/1989  | Tsuo et al.      |         |
| 4,935,345 | A |   | 6/1990  | Guilbeau et al.  |         |
| 4,936,877 | A |   | 6/1990  | Hultquist et al. |         |
| 5,047,352 | A |   | 9/1991  | Stetter et al.   |         |
| 5,054,309 | A |   | 10/1991 | Mettes et al.    |         |
| 5,118,945 | A | * | 6/1992  | Winschuh et al.  | 250/341.4 |

(Continued)

OTHER PUBLICATIONS

Adrian, Peter, "Sensor industry developments and trends", "Sensor Business Digest", Oct. 2001, Publisher: Vital Information Publication.

(Continued)

*Primary Examiner* — Carol S Tsai
(74) *Attorney, Agent, or Firm* — Steven J. Hultquist; Hultquist IP; Chih-Sheng Lin

(57) ABSTRACT

A process system adapted for processing of or with a material therein. The process system includes: a sampling region for the material; an infrared photometric monitor constructed and arranged to transmit infrared radiation through the sampling region and to responsively generate an output signal correlative of the material in the sampling region, based on its interaction with the infrared radiation; and process control means arranged to receive the output of the infrared photometric monitor and to responsively control one or more process conditions in and/or affecting the process system.

20 Claims, 1 Drawing Sheet

U.S. PATENT DOCUMENTS

| | | | |
|---|---|---|---|
| 5,129,412 A | 7/1992 | Hendry | |
| 5,200,023 A * | 4/1993 | Gifford et al. | 216/59 |
| 5,239,856 A | 8/1993 | Mettes et al. | |
| 5,279,146 A | 1/1994 | Asano et al. | |
| 5,282,473 A | 2/1994 | Braig et al. | |
| 5,367,167 A | 11/1994 | Keenan | |
| 5,376,409 A | 12/1994 | Kaloyeros et al. | |
| 5,403,089 A | 4/1995 | Kuo et al. | |
| 5,404,125 A | 4/1995 | Mori et al. | |
| 5,436,457 A | 7/1995 | Tomita | |
| 5,464,983 A | 11/1995 | Wang | |
| 5,470,390 A | 11/1995 | Nishikawa et al. | |
| 5,508,934 A * | 4/1996 | Moslehi et al. | 700/121 |
| 5,518,528 A | 5/1996 | Tom et al. | |
| 5,570,743 A | 11/1996 | Padgett et al. | |
| 5,589,689 A | 12/1996 | Koskinen | |
| 5,594,248 A | 1/1997 | Tanaka | |
| 5,641,245 A | 6/1997 | Pemberton et al. | |
| 5,650,624 A | 7/1997 | Wong | |
| 5,707,500 A * | 1/1998 | Shimamura et al. | 204/298.03 |
| 5,721,430 A | 2/1998 | Wong | |
| 5,782,974 A | 7/1998 | Sorensen et al. | |
| 5,815,396 A * | 9/1998 | Shimamura et al. | 700/123 |
| 5,826,607 A | 10/1998 | Knutson et al. | |
| 5,834,777 A | 11/1998 | Wong | |
| 5,887,611 A | 3/1999 | Lampotang et al. | |
| 5,962,854 A | 10/1999 | Endo | |
| 5,967,992 A | 10/1999 | Canfield | |
| 6,045,257 A | 4/2000 | Pompei et al. | |
| 6,050,283 A | 4/2000 | Hoffman et al. | |
| 6,067,840 A * | 5/2000 | Chelvayohan et al. | 73/23.2 |
| 6,070,600 A | 6/2000 | Grootegoed et al. | |
| 6,089,027 A | 7/2000 | Wang et al. | |
| 6,171,641 B1 * | 1/2001 | Okamoto et al. | 427/8 |
| 6,190,436 B1 | 2/2001 | Ji et al. | |
| 6,348,650 B1 | 2/2002 | Endo et al. | |
| 6,370,950 B1 | 4/2002 | Lammerink | |
| 6,406,555 B1 | 6/2002 | Grootegoed et al. | |
| 6,453,924 B1 * | 9/2002 | Wang et al. | 137/1 |
| 6,469,303 B1 | 10/2002 | Sun et al. | |
| 6,612,317 B2 | 9/2003 | Costantini et al. | |
| 6,617,175 B1 | 9/2003 | Arno | |
| 6,631,334 B2 | 10/2003 | Grosshart | |
| 6,649,994 B2 | 11/2003 | Parsons | |
| 6,689,252 B1 * | 2/2004 | Shamouilian et al. | 204/157.15 |
| 6,694,800 B2 | 2/2004 | Weckstrom et al. | |
| 6,772,781 B2 | 8/2004 | Doty et al. | |
| 6,780,319 B1 | 8/2004 | Thieblin et al. | |
| 6,810,821 B2 | 11/2004 | Chan | |
| 6,821,795 B2 | 11/2004 | Arno | |
| 6,828,172 B2 | 12/2004 | Chavan et al. | |
| 6,909,093 B2 | 6/2005 | Sato et al. | |
| 6,909,973 B2 | 6/2005 | Arno | |
| 6,953,731 B2 | 10/2005 | Shinriki et al. | |
| 7,009,267 B2 | 3/2006 | Honboh | |
| 7,011,614 B2 | 3/2006 | Arno | |
| 7,033,542 B2 | 4/2006 | Archibald et al. | |
| 7,058,519 B2 | 6/2006 | Arno | |
| 7,063,097 B2 | 6/2006 | Arno et al. | |
| 7,080,545 B2 * | 7/2006 | Dimeo et al. | 73/31.05 |
| 7,122,797 B2 * | 10/2006 | Guo et al. | 250/338.1 |
| 7,129,519 B2 | 10/2006 | Arno | |
| 7,172,918 B2 | 2/2007 | Arno | |
| 7,325,560 B2 | 2/2008 | Arno et al. | |
| 7,351,976 B2 | 4/2008 | Arno | |
| 7,373,257 B2 | 5/2008 | Arno | |
| 7,711,496 B2 | 5/2010 | Arno | |
| 7,723,685 B2 | 5/2010 | Arno | |
| 2002/0048213 A1 | 4/2002 | Wilmer et al. | |
| 2002/0051132 A1 | 5/2002 | Ohno et al. | |
| 2002/0168289 A1 | 11/2002 | McVey | |
| 2004/0007180 A1 | 1/2004 | Yamasaki et al. | |
| 2004/0038442 A1 | 2/2004 | Kinsman | |
| 2004/0050326 A1 | 3/2004 | Thilderkvist et al. | |
| 2004/0058488 A1 | 3/2004 | Arno | |
| 2004/0113080 A1 | 6/2004 | Arno | |
| 2004/0121494 A1 | 6/2004 | Arno | |
| 2005/0006799 A1 | 1/2005 | Gregg et al. | |
| 2005/0211555 A1 | 9/2005 | Archibald | |
| 2006/0219923 A1 | 10/2006 | Uchida et al. | |
| 2006/0237061 A1 | 10/2006 | Arno et al. | |
| 2006/0263916 A1 | 11/2006 | Arno | |

OTHER PUBLICATIONS

IEEE, "The Authoritative Dictionary of IEEE Standard Terms, Seventh Edition", Jan. 2001, p. 1174 Publisher: The Institute of Electrical and Electronics Engineers, Inc.

Perry, R.H., et al., "Perry's Chemical Engineers' Handbook (7th Edition)", 1997, pp. Secs. 6, 8, 16, 18, Publisher: McGraw-Hill, Published in: New York, NY.

Schilz, Jurgen, "Applications of thermoelectric infrared sensors (thermopiles): Gas detection by infrared absorption; NDIR", "Thermophysica Minima", Aug. 22, 2000, Publisher: PerkinElmer.

Thermometrics Global Business, "Application note of thermopile sensors (Rev.02)", 2000, pp. 1-9.

Wilks, Paul A., "The birth of infrared filtometry", "Spectroscopy Showcase", accessed at www.spectroscopyonline.com, Mar. 2002, p. 14.

* cited by examiner

PHOTOMETRICALLY MODULATED DELIVERY OF REAGENTS

CROSS-REFERENCE TO RELATED APPLICATIONS

This is a continuation of U.S. patent application Ser. No. 12/120,101 filed May 13, 2008, issuing as U.S. Pat. No. 7,711,496 on May 4, 2010, which in turn is a continuation of U.S. Pat. application Ser. No. 11/445,755 filed Jun. 2, 2006, issued May 13, 2008 as U.S. Pat. No. 7,373,257, which is a continuation of U.S. patent application Ser. No. 11/157,760 filed Jun. 21, 2005, issued Jun. 6, 2006 as U.S. Pat. No. 7,058,519, which in turn is a continuation of U.S. patent application Ser. No. 10/641,576 filed Aug. 14, 2003, issued Jun. 21, 2005 as U.S. Pat. No. 6,909,973, which in turn is a continuation-in-part of U.S. patent application Ser. No. 10/402,759 filed Mar. 28, 2003, issued Jun. 20, 2006 as U.S. Pat. No. 7,063,097. The disclosures of all such applications are hereby incorporated herein by reference, in their respective entireties.

FIELD OF THE INVENTION

The present invention relates to apparatus and method for photometrically modulating the delivery of reagent, e.g., in a semiconductor manufacturing operation including processing of or with such reagent. In a specific aspect, the invention relates to supply of reagent gas deriving from solid and/or liquid sources.

DESCRIPTION OF THE RELATED ART

The semiconductor industry uses a wide variety of reagent gases in applications where the source materials for such reagent gases are solid and/or liquid in character. Such source materials may be highly toxic or hazardous and the dosage of active gas species may in some instances be very small.

When solid and/or liquid source materials are employed, metering the delivery of such non-gaseous materials to a semiconductor processing tool is difficult. Typically, the non-gaseous material is bubbled or swept from a vessel containing the material, by means of a carrier gas that is flowed through the vessel to entrain the vapor of the source material. The resulting carrier gas/active material vapor is then transported as a feed gas stream to the semiconductor tool.

The feed gas stream is flowed to the tool through flow circuitry including lines that typically are heated to prevent condensation and/or freezing of the reagent in the piping, valving, etc. of such flow circuitry.

In design and construction of the semiconductor process system including such tool and the delivery system for the solid and/or liquid source material, it is often necessary to rely on published vapor pressure values for the source material in order to estimate the delivery rate of the source material. Vapor pressure curves in the literature, however, relate to steady state conditions involving vapor-saturated streams. They do not take into account time-varying fluctuations in source material delivery rate, such as may be attributable to (i) changes in liquid levels in the system that may result in non-saturated vapor streams, (ii) concentration spikes that can occur during initial opening of carrier gas valves, (iii) changes in the rate of vaporized material deriving from changes in available surface area of solid source materials, (iv) losses of transported source material due to condensation of the material from the feed stream on cold spots in the flow circuitry, (v) thermal degradation of source material in regions of the flow circuitry or in other process system components that are heated to temperatures above the decomposition temperature of the source material, and (vii) fluctuations in carrier gas flow rates that result in corresponding changes of concentration and delivered amount of the source material.

The foregoing problems involving use of solid and/or liquid source materials has resisted solution, and pose continuing obstacles to the successful utilization of solid and/or liquid source materials for industrial process use, such as in semiconductor manufacturing processes, in which metalorganic compounds and a wide variety of other reagent materials are of non-gaseous form, and require volatilization, vaporization, sublimation or similar operations to provide gaseous or vapor forms of the material to the process for use therein.

SUMMARY OF THE INVENTION

The present invention relates to apparatuses and methods for photometrically modulating the delivery of reagents, such as may derive from solid and/or liquid sources.

In one aspect, the invention relates to a system adapted to supply a gaseous reagent species to a gaseous reagent species-utilizing manufacturing process region, the system comprising:

(a) a sampling region for analyzing the gaseous reagent species;
(b) a monitor in sensory communication with the sampling region, the monitor being constructed and arranged to responsively generate an output signal correlative of presence or concentration of the gaseous reagent species in the sampling region; and
(c) a process controller arranged to receive the output of the monitor and to responsively control one or more process conditions in and/or affecting the gaseous species-utilizing manufacturing process region.

In another aspect, the invention relates to a gaseous reagent species supply system comprising:

a sampling region for analyzing a gaseous reagent species;
an infrared radiation source arranged to emit infrared radiation into the sampling region;
a photometric detector arranged to receive infrared radiation from the sampling region and responsively generate an output signal correlative of presence or concentration of the gaseous reagent species in the sampling region;
at least one infrared radiation filter element optically coupled between the infrared radiation source and the photometric detector; and
a process controller arranged to receive the output of the detector and to responsively control one or more process conditions in and/or affecting the gaseous species-utilizing manufacturing process region.

In another aspect, the invention relates to a system for supplying gaseous reagent material subject to degradation, the system comprising:

a sampling region for analyzing gaseous reagent material;
a photometric monitor arranged to receive radiation from the sampling region and responsively generate an output signal correlative of presence or concentration of any of (i) at least one species of said gaseous reagent material, and (ii) at least one decomposition by-product of said gaseous reagent material or a species thereof; and
a control element adapted to receive the output signal to determine whether degradation of gaseous reagent exceeds a predetermined level.

In another aspect, the invention relates to a process system adapted for processing of or with a material therein, said process system comprising:
   a sampling region for the material;
   an infrared photometric monitor constructed and arranged to transmit infrared radiation through the sampling region and to responsively generate an output signal correlative of the material in the sampling region, based on its interaction with the infrared radiation; and
   process control means arranged to receive the output of the infrared photometric monitor and to responsively control one or more process conditions in and/or affecting the process system.

Another aspect of the invention relates to a method of operating a process including processing of or with a material, such method comprising exposing the material to infrared radiation and responsively generating with an infrared photometric monitor an output correlative of the material, based on its interaction with the infrared radiation; and controlling one or more conditions in and/or affecting the process, in response to the output.

Other aspects, features and embodiments will be more fully apparent from the ensuing disclosure and appended claims.

DETAILED DESCRIPTION OF THE INVENTION AND PREFERRED EMBODIMENTS THEREOF

Figure 1:
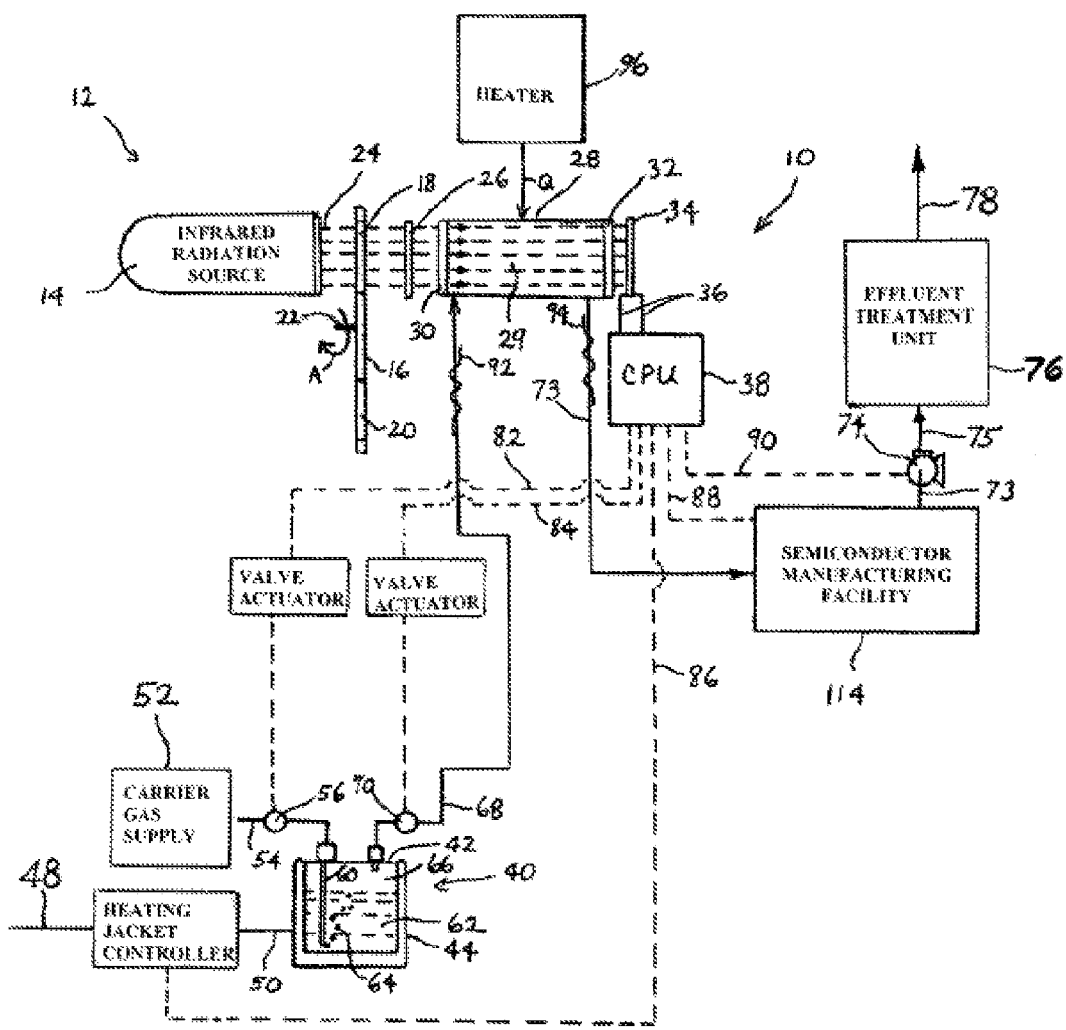
FIG. 1 is a schematic representation of a semiconductor manufacturing process system including photometrically modulated delivery of reagent from a non-gaseous source material, according to one embodiment of the present invention.

The disclosures of U.S. patent application Ser. No. 11/157,760 filed Jun. 21, 2005, U.S. patent application Ser. No. 10/402,759 filed Mar. 28, 2003, and U.S. patent application Ser. No. 10/140,848 filed May 8, 2002 (issued as U.S. Pat. Nos. 7,058,519, 7,063,097, and 6,617,175, respectively) are hereby incorporated herein by reference in their respective entireties, for all purposes.

The present invention relates to utilization of an infrared photometer in a metering arrangement for delivery of reagent, which is useful for delivery of reagent to a process from a non-gaseous source material. The infrared photometer in such arrangement operates as a mass flow meter permitting an output from the infrared photometer to be employed for responsively controlling one or more process conditions in and/or affecting the process system.

More specifically, an infrared photometric monitor is constructed and arranged to transmit infrared radiation through a sampling region, such as a gas cell, and to responsively generate an output correlative of the material in the sampling region, based on its interaction with the infrared radiation.

The process system in addition to a gas-utilizing facility, such as a semiconductor manufacturing facility, e.g., a semiconductor manufacturing tool, or other process unit adapted for processing of or with the monitored material therein, advantageously includes a source for such material providing same in gaseous form for monitoring and subsequent utilization.

The source means may comprise a storage and dispensing vessel for the material, or a synthesis or generating unit for such material, or other suitable supply containers, bulk storage facilities, or the like. The material itself may be in an initially gaseous form, but in a preferred aspect, described more fully hereinafter, the invention is advantageously employed with materials that are in an initially non-gaseous form, e.g., in a liquid state and/or a solid state. The invention thus is amenable to implementation for metered delivery of reagents deriving from source materials that are vaporizable, sublimable, volatilizable, atomizable or otherwise able to be delivered in a gaseous form. The term "gaseous" in such context includes gases as well as vapors.

Infrared photometers usefully employed in the practice of the invention can be of any suitable type including an infrared radiation source and detector elements and associated componentry, e.g., infrared radiation modulation components. Illustrative IR photometers include the CLEANSENS® NDIR photometer commercially available from CS Clean Systems Inc. (Fremont, Calif., USA), the MCS 100E IR photometer commercially available from SICK AG (Waldkirch, Germany) and the PIR3502 Multiwave Process Photometer commercially available from ABB USA (Norwalk, Conn., USA).

The IR photometric monitor can be installed in-line between the material source and the process facility utilizing the gaseous reagent being monitored. In application to a semiconductor manufacturing facility, the IR photometric monitor can be situated in-line in the flow circuitry between a chemical vapor deposition reactor and a liquid material vaporizer or bubbler. Where the flow circuitry coupled with the IR photometric monitor is heated to prevent condensation or freezing of the gaseous reagent being monitored, the IR photometric monitor can be heated to a temperature in the same temperature regime as the flow circuitry.

By such arrangement, the IR photometric monitor provides a time-dependent concentration profile of the material delivered to the gas-utilizing facility. The IR photometric monitor enables concentration of the material of interest to be tracked in real time in a qualitative and quantitative mode. The IR photometric monitor can be arranged to monitor the reagent species of interest, as well as one or more decomposition by-products of such reagent species, thereby providing the capability of detecting unwanted degradation of the reagent, so that process conditions and operation can be responsively altered to suppress any significant decomposition from occurring, when changes in process variables or settings would otherwise cause such degradation to occur.

The output of the IR photometric monitor can be used to control delivery parameters such as carrier gas flow rates, vaporizer temperatures, pressures, etc., so that a desired delivery rate of the reagent of interest can be achieved and maintained even under fluctuations in process conditions and operating modes.

Referring now to the drawing of FIG. 1, there is illustrated a schematic representation of a semiconductor manufacturing process system 10 including photometrically modulated delivery of reagent from a non-gaseous source material, according to one embodiment of the present invention.

The semiconductor manufacturing process system 10 as illustrated includes an infrared photometric monitor 12 and a semiconductor manufacturing facility 114. The semiconductor manufacturing facility 114 may comprise a semiconductor manufacturing tool such as a chemical vapor deposition (CVD) reactor, an ion implantation chamber, a lithotracks unit, or other processing unit in which a reagent in gaseous form is used.

The gaseous form reagent is supplied to the semiconductor manufacturing facility 114 from a reagent material source 40.

Reagent material source 40 includes a bubbler vessel 42 containing a source material 62 in liquid form. The bubbler vessel 42 is disposed in a heating jacket 44 that is coupled by electrical line 50 to the heating jacket controller 46 that in turn is connected by power line 48 to a suitable power source. The heating jacket controller thus is arranged to vary the extent of resistive heating of the vessel 42 by the heating jacket, by correspondingly varying the current flowed in line 50 to the heating jacket 44.

The liquid 62 in vessel 42 is contacted with a gas in the form of bubbles 64 by flow of carrier gas, e.g., helium, argon, nitrogen, hydrogen, or other suitable single component or multi-component carrier medium, from carrier gas supply 52 (e.g., a compressed gas cylinder, bulk gas storage tank, or the like) in carrier gas feed line 54 containing flow control valve 56 therein to the diptube 60. The diptube 60 is open-ended at its lower extremity, thereby permitting the carrier gas to bubble through the non-gaseous source material 62 so as to entrain the source material in the carrier gas.

The carrier gas entraining the source material therein disengages from the liquid 62 in the headspace 66 of the vessel 42, and is discharged from the vessel in line 68 as a feed stream containing the source material and the carrier gas. The feed stream flows in line 68, containing flow control valve 70 therein, and traced with a heat tracing element 92, to the gas sampling chamber 29 of the IR photometric monitor 12. The gas sampling chamber 29 is bound by wall 28 and arranged to be heated by heater 96, to provide an input heat flux denoted schematically by arrow Q.

From the gas sampling chamber 29, the feed stream flows in delivery line 73, traced with heat tracing element 94, to the semiconductor manufacturing facility 114.

By this arrangement, involving heat tracing of the flow circuitry lines 68 and 73, and heating of the gas sampling chamber 29 by the heater 96, the temperature of the feed stream is maintained at a temperature level that ensures that no condensation of the source material takes place in the flow circuitry or the gas sampling chamber.

In the semiconductor manufacturing facility 114, the reagent material is utilized, e.g., as a precursor from which a layer of metal, dielectric, insulator, is deposited under appropriate deposition conditions therefor, or in other manner as a process gas, cleaning fluid, etc. Effluent gas from the semiconductor manufacturing facility 114, which may derive at least in part from the reagent material, is discharged from the semiconductor manufacturing facility 114 in line 73 and flowed to effluent pump 74.

From pump 74, the effluent flows in line 75 to effluent treatment unit 76 for abatement of hazardous species therein, e.g., by scrubbing (wet and/or dry scrubbing), catalytic oxidation, incineration, chemical treatment, or the like. From the effluent treatment unit 76, the final treated effluent is discharged from the process system in vent line 78.

The IR photometric monitor 12 comprises a source of infrared radiation 14 whose output radiation 24 is directed along a path illustratively shown in dashed line representation. The output radiation 24 is modulated by diaphragm wheel 16 having openings 18 and 20 therein. The rotation of the wheel 16 thereby permits the radiation to pass through opening 18 or 20, or alternatively be blocked by the opaque portions of the wheel intermediate the openings 18 and 20. The wheel is rotatable by means of axle 22, which may be operatively coupled with suitable drive means, e.g., an electric motor, generator, gearing assembly, power take-off assembly, flywheel, etc., to effect rotation of the wheel 16 in the direction indicated by arrow A in FIG. 1.

The modulated radiation passes through an interference filter 26 that is transmissive of radiation of a specific frequency range. The resulting infrared radiation enters the sampling chamber 29 through inlet window 30 and interacts with the feed stream introduced into the chamber in line 68, thereby altering the radiation so that the radiation passing out of the sampling chamber 29 through exit window 32 to detector 34 differs from the radiation passing into the chamber through inlet window 30, in a manner that is characteristic of the presence of the reagent species in the feed stream at that point in time. The inlet and exit windows 30 and 32 are formed of IR-transmissive material, such as for example zinc selenide or other suitable material.

The detector 34 of the IR photometric monitor is coupled by terminals 36 to the central processor unit (CPU) 38, to transmit to the CPU a signal that is correlative of the reagent species of interest and its concentration in the feed stream.

The CPU thus is inputted a signal from the IR photometric monitor that is indicative of the presence and amount of the reagent species of interest. The CPU may comprise any suitable means such as a programmable general purpose digital computer, microprocessor, logic unit, integrated circuitry, etc. that is effective for signal processing of the IR photometric monitor signal to produce an output for controlling one or more process conditions in and/or affecting the process system.

In the FIG. 1 system, the CPU is shown as being illustratively operatively linked for control purposes to valve actuator 58 of flow control valve 56, by signal transmission line 82; to valve actuator 72 of flow control valve 70, by signal transmission line 84; to the heating jacket controller 46 by signal transmission line 86; to the semiconductor manufacturing facility 114 by signal transmission line 88; and to the pump 74 by the signal transmission line 90.

By these respective control linkages, which may be used singly, alternatively, or in various combinations, the photometric monitor and associated control assembly can be operated to photometrically sense the concentration of the reagent species of interest in the feed stream and to responsively adjust (i) the flow rate of carrier gas flowed to the bubbler, (ii) the flow rate of the feed stream comprising the carrier gas and the reagent species that is flowed to the sampling chamber and the downstream gas-utilizing process, (iii) the heating of the liquid source material in the bubbler, (iv) any of the tool settings, process conditions, etc. in the semiconductor manufacturing facility, and/or (v) the pumping rate of the pump used to flow the effluent from the semiconductor manufacturing facility to the effluent treatment unit. Additionally, or alternatively, the CPU may be arranged to control the heating of material in gaseous or non-gaseous form in the process system, e.g., by controlling rate of heat input to the heat tracing elements and the sampling chamber.

It will be appreciated that the specific control linkages shown in FIG. 1 are of illustrative character only, and that the monitoring and control system and methodology of the invention can be widely varied to control any specific devices, elements, process units, process conditions, set points, alarm settings, operational modes, cycle times, emergency procedures, etc. based on the photometrically determined presence of the reagent species of interest.

Thus, the system is arranged so that the gas-utilizing process is controlled in response to the photometric sensing of the reagent species of interest, thereby permitting optimal process operation to be achieved and maintained throughout the temporal duration of the gas-utilizing process.

It will be further recognized that although the illustrative embodiment of FIG. 1 has been shown as comprising a single IR photometer detection arrangement, the invention is not thus limited, and that the invention contemplates the provision of IR photometric capability for real-time contemporaneous sensing of multiple specific components of a gaseous feed stream, and that the CPU may be programmatically arranged to accommodate such multi-species monitoring by suitable control algorithms and protocols, so as to provide a highly integrated monitoring and control functionality sensitive to very small variations of any of a number of components in the source material.

As will be apparent from the foregoing, the present invention provides the capability for monitoring and control of a gas-utilizing process system that permits the efficient use of non-gaseous source materials for generating gaseous reagent species, thereby obviating the numerous deficiencies of prior art approaches for using non-gaseous source materials, as discussed in the Background of the Invention section hereof.

While the invention has been described herein with reference to specific aspects, features and embodiments, it will be recognized that the invention is not thus limited, but is susceptible to implementation in numerous other variations, modifications, and alternative embodiments. Accordingly, the invention is intended to be broadly construed as encompassing such variations, modifications and alternative embodiments, within the spirit and scope of the invention as hereinafter claimed.

What is claimed is:

1. A method of performing process control in a manufacturing process, the method comprising
    monitoring a gaseous material using a system adapted to supply the gaseous material to a gaseous material-utilizing manufacturing process region, the system comprising: (a) a sampling region for analyzing the gaseous material; (b) a monitor in sensory communication with the sampling region, the monitor being constructed and arranged to responsively generate an output signal correlative of presence or concentration of any of (i) at least one species of said gaseous material, and (ii) at least one decomposition by-product of said gaseous material or a species thereof; and (c) a process controller arranged to receive the output signal of the monitor and to responsively control one or more process conditions in and/or affecting the gaseous material-utilizing manufacturing process region, and
    controlling one or more process conditions in and/or affecting the gaseous material-utilizing manufacturing process region responsive to the output signal of the monitor.

2. The method of claim 1, wherein the monitor comprises an infrared radiation source arranged to emit infrared radiation into the sampling region; and a photometric detector arranged to receive infrared radiation from the sampling region.

3. The method of claim 2, wherein the monitor further comprises at least one infrared radiation filter element optically coupled between the infrared radiation source and the photometric detector.

4. The method of claim 1, wherein the monitor comprises a photometric monitor.

5. The method of claim 4, wherein the process controller is adapted to receive the output signal to determine whether degradation of gaseous material exceeds a predetermined level.

6. The method of claim 2, wherein monitoring the gaseous material comprises photometrically detecting radiation emitted into the sampling region and responsively generating an output signal correlative of presence or concentration of any of (i) at least one species of said gaseous reagent material, and (ii) at least one decomposition by-product of said gaseous reagent material or a species thereof.

7. The method of claim 1, further comprising utilizing the process controller to suppress degradation of the gaseous responsive to the output signal from the monitor.

8. The method of claim 1, wherein the gaseous material is generated from a non-gaseous material.

9. The method of claim 8, wherein the non-gaseous material is transformed into the gaseous material by vaporizing, subliming, volatilizing, or atomizing.

10. The method of claim 1, wherein gaseous material further comprises a solid or a liquid.

11. The method of claim 1, wherein the monitor comprises an infrared photometric monitor constructed and arranged to transmit infrared radiation through the sampling region and to responsively generate an output signal correlative of presence or concentration of the gaseous reagent species in the sampling region, based on its interaction with the infrared radiation.

12. The method of claim 1, wherein said process controller is adapted to control a delivery parameter selected from gaseous material flow rate, vaporizer temperature, pressure and combinations thereof.

13. The method of claim 1, further comprising supplying the gaseous material to the gaseous material-utilizing manufacturing process region from a source vessel.

14. The method of claim 1, further comprising flow circuitry for the gaseous material.

15. The method of claim 14, wherein a portion of the flow circuitry is heated.

16. The method of claim 1, wherein the sampling region comprises a gas cell, and the gas cell is heated to prevent condensation.

17. The method of claim 1, wherein the process controller controls flow rate of the gaseous material, temperature of the gaseous material, or utilization of the gaseous material in the gaseous-material utilizing manufacturing process region.

18. The method of claim 1, comprising controlling gaseous material flow rate, temperature, or utilization in the gaseous-material utilizing manufacturing process region.

19. The method of claim 2, wherein the process controller is adapted to control a delivery parameter selected from gaseous material flow rate, temperature, pressure and combinations thereof.

20. The method of claim 2, comprising controlling gaseous material flow rate, temperature, or utilization in the gaseous-material utilizing manufacturing process region.

* * * * *

UNITED STATES PATENT AND TRADEMARK OFFICE
CERTIFICATE OF CORRECTION

PATENT NO. : 7,925,450 B2
APPLICATION NO. : 12/773666
DATED : April 12, 2011
INVENTOR(S) : Jose I. Arno Page 1 of 1

It is certified that error appears in the above-identified patent and that said Letters Patent is hereby corrected as shown below:

Column 8, lines 13-14 (claim 7): "degradation of the gaseous" should be -- degradation of the gaseous material --.

Signed and Sealed this
Twenty-eighth Day of June, 2011

David J. Kappos
*Director of the United States Patent and Trademark Office*